United States Patent [19]
Hayakawa et al.

[11] Patent Number: 4,902,673
[45] Date of Patent: Feb. 20, 1990

[54] ENHANCING GROWTH OF BIFIDOBACTERIA USING SOYBEAN EXTRACT

[75] Inventors: Kunihiko Hayakawa, Tokyo; Teruhisa Masai; Yasuyuki Yoshida, both of Kanagawa; Takanobu Shibuta; Hiroshi Miyazaki, both of Tokyo, all of Japan

[73] Assignee: The Calpis Food Industry Co., Ltd., Tokyo, Japan

[21] Appl. No.: 270,469

[22] Filed: Nov. 9, 1988

Related U.S. Application Data

[63] Continuation of Ser. No. 943,206, Dec. 15, 1986, abandoned.

[30] Foreign Application Priority Data

Dec. 27, 1985 [JP] Japan ................. 60-292425

[51] Int. Cl.$^4$ ............. A61K 35/78; C07K 3/02; C07K 3/28
[52] U.S. Cl. ............................. 514/21; 514/8; 514/2; 530/350; 530/378; 530/377; 530/825; 530/414; 530/424; 530/422; 435/252.1; 435/252; 435/244; 435/253.6
[58] Field of Search ............. 530/378, 350, 370, 377, 530/825, 395, 414, 417, 418, 422, 424; 424/195.1; 435/244, 253, 252; 514/8, 21

[56] References Cited

U.S. PATENT DOCUMENTS

| | | | |
|---|---|---|---|
| 3,207,744 | 9/1965 | O'Hara et al. | 530/378 |
| 3,682,646 | 8/1972 | De Paolis | 530/378 |
| 3,926,940 | 12/1975 | Circle et al. | 530/378 |
| 4,113,716 | 9/1978 | Gomi et al. | 530/378 |
| 4,119,435 | 10/1978 | Nakao et al. | 530/378 |
| 4,212,798 | 7/1980 | Satou et al. | 530/378 |
| 4,396,631 | 8/1983 | Adachi et al. | 530/378 |

OTHER PUBLICATIONS

Nash et al, J. Agr. Food Chem. 15(1), 102–108, (1967).
Chem. Abst. 103 (17):140654m (for Yakult Honsha Co, Ltd., JP60/66,978, Apr. 17, 1985).
Chem. Abst. 100:64645e (for Tanaka et al, Bifidobact. Microflora, (1983), 2(1), 17–24).
C.A. 96:179446g (for Yakult Honsha Co., (Neth) NO 80/04,210, Feb. 16, 1982).
C.A. 93:239847p (for Yakult Honsha Co, JP 80,104,885, Aug. 11, 1980).

*Primary Examiner*—Margaret Moskowitz
*Assistant Examiner*—Jeff Kushan
*Attorney, Agent, or Firm*—Browdy and Neimark

[57] ABSTRACT

A bidifobacteria growth promoter contained in soybeans is extracted from defatted soybeans with an aqueous solution of alcohol.

5 Claims, 1 Drawing Sheet

ENHANCING GROWTH OF BIFIDOBACTERIA USING SOYBEAN EXTRACT

This application is a continuation of application Ser. No. 943,206, filed Dec. 15, 1986, now abandoned.

FIELD OF INDUSTRIAL APPLICATION

This invention relates to a method for the preparation of a growth promoter for bacteria belonging to the genus Bifidobacterium, i.e., bifidobacteria.

Bifidobacteria are generally believed to be physiologically desirable for men from infants to adults. It is considered that they are particularly effective in preventing intestinal infection, reinforcing immune functions, controlling enteral putrefaction and improving the metabolism of proteins and vitamins.

Recently it has been attempted to administer bifidobacteria per se in the field of clinical medicine since these bacteria are believed to be effective in the treatment of various diseases including enterogastric disorders, hepatic disorders, dermatoses, allergoses and microbial substitution in infants, children, adults and aged people.

Further there have been marketed food products containing bifidobacteria in the form of yoghurt or tablet candy in order to utilize the advantageous properties of the same.

From a medical viewpoint, it is believed that the presence of a bifidus flora is effective in preventing diseases and/or accelerating recovery therefrom not only in infants but also in adults and aged people. Therefore it is required to habitually maintain an enteral bifidobacterial count on a high level.

A temporary increase in the bifidobacterial count may be achieved only by orally administering bifidobacteria continuously. However the bifidobacteria thus incorporated in the body would be soon excreted from the body once the administration is suspended. Thus it is difficult to maintain the enteral bifidobacterial count on a high level only by orally administering the same.

Thus it is required to achieve an enteral environment where bifidobacteria can reside and grow. Therefore it has been attempted to maintain the enteral bifidobacterial count on a high level by orally administering a growth promoter(s) for bifidobacteria optionally with bifidobacteria.

PRIOR ART

It is known that soybean milk is effective on the growth of bifidobacteria (cf. Japanese Patent Laying-Open Nos. 142566/1976 and 85390/1980). However these references do not disclose which component(s) of soybean are effective.

Japanese Patent Laying-Open Nos. 179064/1984 and 66978/1985 disclose each a method for the preparation of a bifidobacteria growth promoter from soybean milk which comprises a step of removing proteins by adding phosphoric or hydrochloric acid to soybean milk; a neutralization step where calcium hydroxide is employed in the presence of calcium chloride; a precipitation step under heating; and a desalting and concentration step.

However neither of these methods is excellent from an industrial viewpoint, since amino acids present in soybean whey are in danger of reacting with sugars during the heating step to thereby decompose sugar compounds. Further these methods are complicated on the whole.

SUMMARY OF THE INVENTION

Under these circumstances, we have examined on the extraction of components effective on bifidobacteria from soybeans. As a result, we have found that a bifidobacterial growth promoter is directly extracted with an aqueous solution of alcohol from defatted soybeans to thereby establish a novel and convenient method for the preparation of the bifidobacteria growth promoter.

The present invention provides a method for the preparation of the bifidobacteria growth promoter which comprises extracting, with an aqueous solution of alcohol, defatted soybeans or a residue obtained by removing fat-soluble components from soybeans by extraction with a fat-dissolving solvent.

The aqueous solution of alcohol as used for the extraction in the present invention may be preferably one having a concentration of 20 to 60% by volume.

The alcohol as used in the present invention may be preferably ethyl or methyl alcohol or a mixture thereof.

MEANS FOR SOLVING THE PROBLEMS

Figure 1:
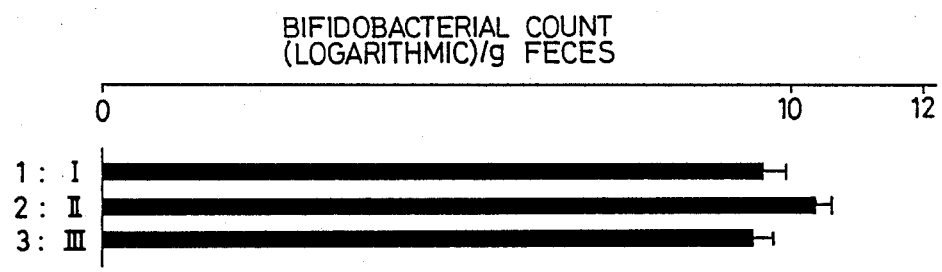
FIG. 1 is a graph which shows changes in the average bifidobacterial count (logarithmic) of five adults per g feces as determined in Test Example 3.

In the present invention, defatted soybeans or soybeans defatted by flaking raw soybeans and extracting fat-soluble components therefrom with a fat-dissolving solvent, e.g., hexane, are employed as starting material. To these defatted soybeans, an aqueous solution of alcohol having a concentration of 20 to 80% by volume, preferably 20 to 60% by volume, is added in an amount five to ten times by weight as much as the defatted soybeans. The resulting mixture is stirred at room temperature or at an elevated temperature (e.g., ca. 60° C.) and the bifidobacteria growth promoter is extracted therefrom. When the extraction is carried out under heating, a temperature of 40° to 80° C., preferably around 60° C., may be employed. However this heating operating may only accelerate the extraction. Thus it is not essential in the present invention.

After the completion of the extraction, insoluble matters in the extract are removed by centrifugation or filtration to thereby give a supernatant.

Then, from the supernatant (i.e., the alcohol-containing extract) the alcohol is removed and removed, and the water of the supernatant is removed to an optional extent. Thus the aimed bifidobacteria growth promoter can be obtained in a concentrated form, i.e., as a concentrated extract containing the bifidobacteria growth promoter.

The concentrated bifidobacteria growth promoter (i.e., the concentrated extract containing the bifidobacteria growth promoter) thus obtained may be formulated into powder by, e.g., spray-drying or lyophilizing.

To further illustrate the present invention, the following Test Examples and Examples will be given.

TEST EXAMPLE 1

*Bifidobacterium longum* ATCC 15707 and *Bifidobacterium breve* ATCC 15701 were cultured each in 200 ml of Brigg's liver broth (cf. Nyugikyo Shiryo, 32 (6), 15 (1983)) at 37° C. for 12 hours. Then each culture liquor was centrifuged and the cells thus collected were suspended in 200 ml of a physiological saline solution (pH 7) containing 0.05% of ascorbic acid to give a starter. Then 2 g of the powdery bifidobacteria growth promoter as prepared in Example 1, 2 g of stachyose or 2 g of raffinose was added to a medium comprising 2 g of proteose peptone (mfd. by Difco), 1 ml of a solution of inorganic salts containing 4% of $MgSO_4.7H_2O$, 0.2% of $FeSO_4.7H_2O$, 0.2% of NaCl and 0.14% of $MnSO_4$, 0.04 g of cysteine hydrochloride and 0.01 g of $CaCO_3$, and the medium was adjusted to a volume of 200 ml with deionized water. After adjusting the pH value of the medium to 7.2 and sterilizing the same, 4 ml of the abovementioned starter was inoculated to this medium and then anaerobically cultured therein at 37° C. for 12 hours. Then an increase in the bacterial count was determined as the optical density (OD) at 630 nm to thereby compared the effects of promoting the growth of each bacterium of the additives. Table 1 shows the result.

TABLE 1

| Strain | | Immediately after inoculation | After culturing at 37° C. for 12 hours | ΔOD |
|---|---|---|---|---|
| B. longum | Bifidobacteria growth promoter of the invention | 0.027 | 0.225 | 0.198 |
| ATCC15707 | Raffinose | 0.024 | 0.074 | 0.050 |
| B. breve | Bifidobacteria growth promoter of the invention | 0.031 | 0.268 | 0.237 |
| ATCC15701 | Stachyose | 0.027 | 0.100 | 0.073 |

Note:
The OD determination is performed by adding 1 ml of the culture medium to 9 ml of a 0.1 N solution of hydrochloric acid, stirring the obtained mixture and measuring the optical density thereof at 630 nm.

Table 1 teaches that the bifidobacteria growth promoter of the present invention shows a significantly higher effect of promoting the growth of bifidobacteria than raffinose or stachyose.

The extraction of sugars from soybeans with alcohols has been already known (cf. "Daizu Tanpakushitsu", translated by Atsuji Watanabe and Kazuo Shibazaki, published by Kenpakusha on June 25, 1971). However, this reference disclosed only the fact that sugars contained in soybeans, such as sucrose, raffinose and stachyose, can be extracted with alcohol.

The result of the above test suggests that the bifidobacteria growth promoter of the present invention contains a growth-promoting substance(s) different from stachyose and raffinose.

TEXT EXAMPLE 2

1-kg portions of defatted soybeans were mixed with 7-l portions of aqueous solutions of ethyl alcohol at concentrations of 0, 20, 40, 60, 80 and 100% by volume. Each mixture thus obtained was stirred at 60° C. for 30 minutes to thereby perform extraction. After filtering insoluble matters off through a Celite filter, the ethyl alcohol in the filtrate was distilled off and the extract was further concentrated. The resulting concentrated extract was then lyophilized to give powder.

Separately B. longum ATCC 15707 was inoculated to 200 ml of the same Brigg's liver broth as the one used in Test Example 1 and anaerobically cultured therein at 37° C. for 12 hours. Then the culture liquor was centrifuged and the cells thus collected were suspended in 200 ml of a physiological saline solution (pH 7.0) containing 0.5% of ascorbic acid to give a starter. 1 g of the lyophilized powder as described above was added to a medium comprising 2 g of the same proteose peptone as the one used in Test Example 1, 1 ml of the same solution of inorganic salts as the one used in Test Example 1, 0.04 g of cysteine hydrochloride and 0.01 g of $CaCO_3$. The medium was adjusted to a volume of 200 ml with deionized water and to a pH value of 7.2 followed by sterilizing. Then 4 ml of the above-mentioned starter was inoculated to this medium and anaerobically cultured therein at 37° C. for 12 hours. After the culture, the pH value, the optical density and the bacterial count in the culture medium were determined.

Table 2 shows the result.

TABLE 2

| Lyophilized powder of the bifidobacteria growth promoter | Immediately after inoculation OD 630 nm | After culturing at 37° C. for 12 hours | | | |
|---|---|---|---|---|---|
| | | pH | OD 630 nm | ΔOD | Viable count (cells/ml) |
| None | 0.021 | 7.23 | 0.023 | 0.002 | $3.2 \times 10^7$ |
| Extract with 0% ethyl alcohol | 0.014 | 6.20 | 0.079 | 0.065 | $1.1 \times 10^8$ |
| Extract with 20% ethyl alcohol | 0.024 | 5.76 | 0.125 | 0.101 | $4.0 \times 10^8$ |
| Extract with 40% ethyl alcohol | 0.027 | 5.71 | 0.141 | 0.114 | $4.1 \times 10^8$ |
| Extract with 60% ethyl alcohol | 0.116 | 5.67 | 0.216 | 0.100 | $2.8 \times 10^8$ |
| Extract with 80% ethyl alcohol | 0.280 | 5.71 | 0.352 | 0.072 | $8.2 \times 10^7$ |
| Extract with 100% ethyl alcohol | 0.321 | 6.51 | 0.381 | 0.060 | $5.9 \times 10^7$ |

Note:
The OD determination is performed by adding 1 ml of the culture medium to 9 ml of a 0.1 N solution of hydrochloric acid, stirring the obtained mixture and measuring the optical density thereof at 630 nm. Bacterial count at the inoculation is $3.3 \times 10^7$/ml (pH 7.2).

Table 2 obviously indicates that remarkable effects of promoting the growth of the bifidobacterium are observed in the lots extracted with ethyl alcohol solutions of 20 to 60% by volume in concentration.

TEST EXAMPLE 3

The lyophilized powder as prepared in Example 1 was administered to five adults in the following manner.

1. The feces of each subject was weighed once a week, i.e., twice in total and the bifidobacterial count therein was determined for two weeks prior to the initiation of the administration.

2. 1.5 g of the lyophilized powder was orally administered to the subject twice a day, i.e., in morning and evening for two weeks. During this administration period, feces of the subject was weighed once a week, i.e. twice in total, and the bifidobacterial count therein was determined.

3. The feces of the subject was weighed once a week, i.e., twice in total and the bifidobacterial count therein was determined for two weeks after the completion of the administration.

Figure 2:
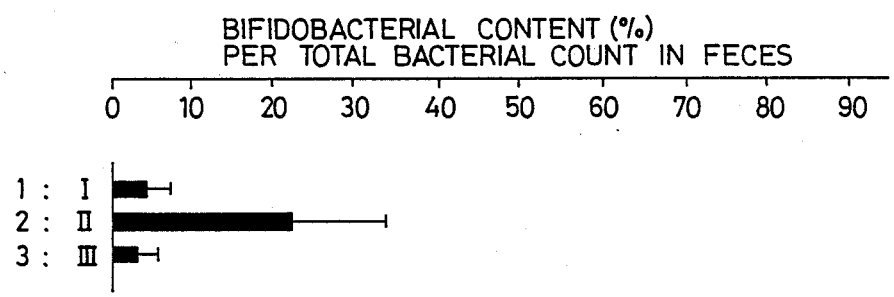
FIG. 2 is a graph which shows changes in the ratio (%) of the bifidobacterial count to the total bacterial count in feces.

FIG. 1 shows the bifidobacterial count (logarithmic) per g of the feces while FIG. 2 shows the bifidobacterial content (%) per total bacterial count in the feces. Each value as listed in these figures is an average of the five subjects.

FIGS. 1 and 2 indicate that the bifidobacteria growth promoter of the present invention promotes the growth of bifidobacteria in adults.

EXAMPLE 1

Soybeans were flaked and fat-soluble components thereof were extracted with hexane to give defatted soybeans. To 1.0 kg of the defatted soybean flakes thus obtained, 7 l of an aqueous solution of ethyl alcohol of a concentration of 60% by volume was added and the resulting mixture was stirred at 60° C. for 30 minutes. Subsequently insoluble matters in the mixture were filtered off and the ethyl alcohol in the filtrate was distilled off under reduced pressure. Thus 1.03 kg of a concentrated extract was obtained. The whole of this extract was lyophilized to give 106 g of a bifidobacteria growth promoter. The obtained product comprised 6.9% of proteins, 2.8% of fats, 82.5% of sugars and 6.3% of ash.

EXAMPLE 2

Defatted soybeans were prepared by flaking soybeans and extracting fat-soluble components thereof with hexane. To 1.0 kg of the defatted soybean flakes thus obtained, 7 l of an aqueous solution of methyl alcohol of a concentration of 50% by volume was added and the resulting mixture was stirred at 60° C. for 30 minutes. Subsequently insoluble matters in the mixture were filtered off and the methyl alcohol in the filtrate was distilled off under reduced pressure. Thus 1.1 kg of a concentrated extract was obtained. The whole of this extract was lyophilized to give 106 g of a bifidobacteria growth promoter. The obtained product comprised 7.5% of proteins, 1.0% of fats, 84.1% of sugars and 6.4% of ash.

EFFECTS OF THE INVENTION

According to the present invention, the bifidobacteria growth promoter contained in soybeans can be readily and efficiently prepared.

Further an enteral environment wherein the residence and growth of bifidobacteria can be promoted can be realized with the use of the bifidobacteria growth promoter obtained by the method of the present invention. It is particularly effective in maintaining the enteral bifidobacteria content on a high level of administer the growth promoter of the present invention together with bifidobacteria.

Thus the present invention is significantly useful in the fields of food and pharmaceuticals to which bifidobacteria are applied.

What is claimed is:

1. A method promoting the growth of bifidobacteria, comprising the steps of culturing bifidobacteria in the presence of a growth promoting amount of a bifidobacteria growth promoter produced by steps including:

mixing defatted soybean flakes with an aqueous solution of alcohol of a concentration of 20 to 80% by volume in the ratio 1:5 to 10 by weight;

stirring the mixture;

obtaining a supernatant alcohol-containing extract by removing insoluble materials from the mixture by filtration or centrifugation; and concentrating the supernatant by distillation under reduced pressure.

2. The method of claim 1, wherein said bifidobacteria growth promoter used in said culturing is applied as a powder which has been produced by drying the resultant concentrated extract by spray-drying or lyophilizing.

3. A method for promoting the growth of bifidobacteria in the digestive system of a subject, comprising the step of:

orally administering a concentrated extract containing a bifidobacteria growth promoter to a patient in an amount effective to significantly promote the growth of bifidobacteria, said concentrated extract having been produced by:

mixing defatted soybean flakes with an aqueous solution of alcohol of a concentration of 20 to 80% by volume in the ratio 1.5 to 10 by weight;

stirring the mixture;

obtaining a supernatant alcohol-containing extract by removing insoluble materials from the mixture by filtration or centrifugation; and concentrating the supernatant by distillation under reduced pressure.

4. A method of promoting the growth of bifidobacteria in a subject, comprising the steps of:

orally administering a bifidobacteria growth promoter to a subject in an amount effective to significantly promote the growth of bifidobacteria, said bifidobacteria growth promoter having been produced by:

mixing defatty soybean flakes with an aqueous solution of alcohol of a concentration of 20 to 80% by volume in the ratio of 1:5 to 10 by weight;

stirring the mixture;

obtaining a supernatant alcohol-containing extract by removing insoluble materials from the mixture by filtration or centrifugation;

concentrating the supernatant by distillation under reduced pressure; and drying the resultant concentrated extract by spray-drying or lyophilizing.

5. The method of claim 1, wherein said culturing is performed in the presence of said concentrated supernatant.

* * * * *